(12) United States Patent
Hsu et al.

(10) Patent No.: US 6,602,912 B2
(45) Date of Patent: *Aug. 5, 2003

(54) TRANSDERMAL ADMINISTRATION OF PHENYLPROPANOLAMINE

(75) Inventors: Tsung-Min Hsu, San Diego, CA (US); Russell Macy, San Marcos, CA (US); Eric C. Luo, Plano, TX (US)

(73) Assignee: Dermatrends, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/738,393

(22) Filed: Dec. 14, 2000

(65) Prior Publication Data

US 2002/0032240 A1 Mar. 14, 2002

Related U.S. Application Data

(63) Continuation-in-part of application No. 09/607,892, filed on Jun. 30, 2000, now abandoned.

(51) Int. Cl.⁷ ........................ A01N 33/02; A61K 31/135
(52) U.S. Cl. ........................................................ 514/653
(58) Field of Search ............................ 424/449; 514/653

(56) References Cited

U.S. PATENT DOCUMENTS

| | | |
|---|---|---|
| 3,028,429 A | 4/1962 | Wilbert et al. |
| 4,289,749 A | 9/1981 | Keith et al. |
| 4,559,222 A * | 12/1985 | Enscore et al. ............ 424/28 |
| 4,639,368 A * | 1/1987 | Niazi et al. ............... 424/48 |
| 4,789,547 A | 12/1988 | Song et al. |
| 4,818,541 A | 4/1989 | Sanderson |
| 4,837,027 A | 6/1989 | Lee et al. |
| 5,019,594 A | 5/1991 | Wurtman |
| 5,021,457 A | 6/1991 | Akin et al. |
| 5,071,657 A | 12/1991 | Oloff et al. |
| 5,075,291 A * | 12/1991 | DuRoss .................... 514/60 |
| 5,096,712 A | 3/1992 | Wurtman et al. |
| 5,260,073 A | 11/1993 | Phipps |
| 5,462,744 A | 10/1995 | Gupte et al. |
| 5,474,783 A | 12/1995 | Miranda et al. |
| 5,498,417 A | 3/1996 | Lhila et al. |
| 5,534,496 A | 7/1996 | Lee et al. |
| 5,573,778 A | 11/1996 | Therriault et al. |
| 5,879,690 A | 3/1999 | Perricone |
| 5,985,317 A | 11/1999 | Venkateshwaran et al. |
| 5,985,860 A | 11/1999 | Toppo |
| 5,989,586 A | 11/1999 | Hsu et al. |
| 5,993,851 A | 11/1999 | Foldvari |
| 6,019,988 A | 2/2000 | Parab et al. |
| 6,019,997 A | 2/2000 | Scholz et al. |
| 6,174,546 B1 | 1/2001 | Therriault et al. |
| 6,204,268 B1 | 3/2001 | Scarborough et al. |
| 6,270,793 B1 | 8/2001 | Van Dyke et al. |

FOREIGN PATENT DOCUMENTS

| | | |
|---|---|---|
| CA | 2006425 | 6/1990 |
| EP | 0316065 | 5/1989 |
| EP | 0374725 | 6/1990 |
| FR | 2692145 | 12/1993 |
| JP | 60222411 | * 11/1985 |
| WO | WO 82/00099 | 1/1982 |

OTHER PUBLICATIONS

Scherzinger et al. (1990), "Steady State Pharmacokinetics and Dose–Proportionality of Phenylpropanolamine in Healthy Subjects," *J. Clin. Pharmacol.* 30(4):372–377.

Aungst et al. (1990), "Contributions of Drug Solubilization, Partitioning, Barrier Disruption, and Solvent Permeation to the Enhancement of Skin Permeation of Various Compounds with Fatty Acids and Amines," *Pharmaceutical Research* 7(7):712–718.

* cited by examiner

*Primary Examiner*—Alton Pryor
(74) *Attorney, Agent, or Firm*—Dianne E. Reed; Reed & Associates

(57) ABSTRACT

Methods and systems are provided for the transdermal administration of racemic phenylpropanolamine, i.e., a mixture of two or more of the four isomers of phenylpropanolamine, (+)-norephedrine, (−)-norephedrine, (+)-norpseudoephedrine, and (−)-norpseudoephedrine. Generally, the racemate will be a mixture of (+)-norephedrine and (−)-norephedrine. The racemic drug is administered along with a permeation enhancer. The permeation enhancer is preferably a basic compound, and optimally is a hydroxide-releasing agent such as sodium hydroxide.

48 Claims, 5 Drawing Sheets

TRANSDERMAL ADMINISTRATION OF PHENYLPROPANOLAMINE

CROSS-REFERENCE TO RELATED APPLICATIONS

This is a continuation-in-part of U.S. Ser. No. 09/607,892, filed Jun. 30, 2000, now abandoned, the disclosure of which is incorporated by reference.

TECHNICAL FIELD

This invention relates generally to the topical and transdermal administration of pharmacologically active agents, and more particularly relates to methods, drug delivery systems and pharmaceutical compositions for transdermal administration of phenylpropanolamine.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10-15 microns thick over most of the body. It is believed to be the high degree of keratinization within these cells as well as their dense packing which creates in most cases a substantially impermeable barrier to drug penetration. With many drugs, the rate of permeation through the skin is extremely low without the use of some means to enhance the permeability of the skin.

In order to increase the rate at which a drug penetrates through the skin, then, various approaches have been followed, each of which involves the use of either a chemical penetration enhancer or a physical penetration enhancer. Physical enhancement of skin permeation includes, for example, electrophoretic techniques such as iontophoresis. The use of ultrasound (or "phonophoresis") as a physical penetration enhancer has also been researched. Chemical enhancers are compounds that are administered along with the drug (or in some cases the skin may be pretreated with a chemical enhancer) in order to increase the permeability of the stratum corneum, and thereby provide for enhanced penetration of the drug through the skin. Ideally, such chemical penetration enhancers (or "permeation enhancers," as the compounds are referred to herein) are compounds that are innocuous and serve merely to facilitate diffusion of the drug through the stratum corneum.

Nevertheless, the number of drugs that can be safely and effectively administered through the skin, without concomitant problems such as irritation and sensitization, remains limited.

The present invention is directed to the transdermal administration of 2-amino-1-phenyl-1-propanol, or "phenylpropanolamine." The drug is described, for example, by Kanfer et al., in *Analytical Profiles of Drug Substances*, vol. 12, K. Florey, Ed. (New York: Academic Press, 1983). Phenylpropanolamine is a sympathomimetic agent that has been used as an anorectic agent, a decongestant, an anxiolytic agent, and as a drug for decreasing fatigue and confusion. See, for example, U.S. Pat. No. 5,019,594 to Wurtman et al., U.S. Pat. No. 5,260,073 to Phipps, and U.S. Pat. No. 5,096,712 to Wurtman.

Phenylpropanolamine has the molecular structure (I)

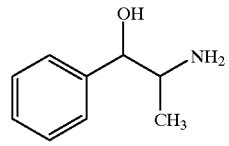

(I)

and, as may be seen contains two chiral centers. Thus, phenylpropanolamine exists as four different isomers, as follows:

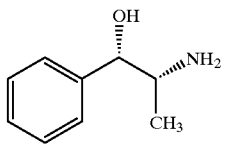

(Ia)

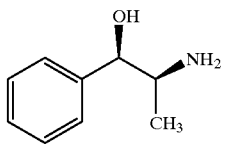

(Ib)

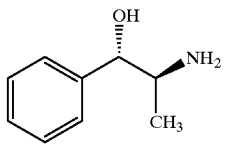

(Ic)

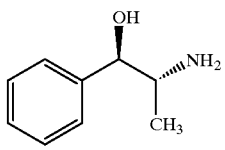

(Id)

Isomers (Ia) through (Id) are generally referred to as (+)-norephedrine, (−)-norephedrine, (+)-norpseudoephedrine, and (−)-norpseudoephedrine, respectively. Generally, isomers (Ib) and (Ic), i.e., (−)-norephedrine and (+)-norpseudoephedrine, are recognized as the more active isomers for most physiological uses. The typical formulation, however, is a racemic mixture of (+)-norephedrine and (−)-norephedrine. This mixture, generally referred to as (±)-phenylpropanolamine (or simply "phenylpropanolamine"), is commercially available for use as an anorectic agent at a dose of about 50–75 mg/day, and as a nasal decongestant at a dose of about 75–150 mg/day.

Currently, phenylpropanolamine is administered orally, in tablets, capsules or syrups. The present invention, however, is directed to the transdermal administration of phenylpropanolamine. There are a number of other advantages to administering phenylpropanolamine transdermally: continuous delivery provides for sustained blood levels of the otherwise short-lived drug (the half-life of phenylpropanolamine is on the order of 3.8 to 4.3 hours—see Scherzinger et al. (1990) *J. Clin. Pharmacol.* 30(4):372–377); there is no first-pass effect; side effects typically associated with oral administration may be substantially avoided; continuous delivery provides for sustained blood levels; the transdermal patch is easily removable if any side effects do occur; and the likelihood of both patient acceptance and patient compliance is significantly improved.

Transdermal administration of phenylpropanolamine has been proposed. In U.S. Pat. No. 4,818,541, transdermal systems are disclosed for delivering phenylpropanolamine to the skin. In the aforementioned patent, however, it is noted that the skin flux of (±)-phenylpropanolamine (i.e., a mixture of (−)-norephedrine and (+)-norephedrine) is only 16 $\mu g/cm^2/hr$, although the skin flux of individual enantiomers was found to be higher. Furthermore, the method of the '541 patent requires neutralization of phenylpropanolamine hydrochloride (i.e., conversion to the free base), the commercially available form of the drug, before incorporation into a transdermal drug delivery system.

Accordingly, there is a need in the art for a way to transdermally administer racemic phenylpropanolamine without being limited by the racemate's low skin flux, and without having to convert phenylpropanolamine hydrochloride to the base form of the drug prior to patch manufacture. The terms "racemic" or "racemate" as used herein refer to a mixture of any two or more of the four isomers of phenylpropanolamine, but typically refer to a mixture of (−)-norephedrine and (+)-norephedrine.

Various compounds for enhancing the permeability of skin are known in the art and described in the pertinent texts and literature. Compounds that have been used to enhance skin permeability include: the sulfoxides dimethylsulfoxide (DMSO) and decylmethylsulfoxide ($C_{10}$MSO); ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); the 1-substituted azacycloheptan-2-ones, particularly 1-n-dodecylcyclazacycloheptan-2-one (available under the trademark Azone® from Nelson Research & Development Co., Irvine, Calif.; see U.S. Pat. Nos. 3,989,816, 4,316,893, 4,405,616 and 4,557,934); alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanol amine, diethanol amine and triethanolamine; terpenes; alkanones; and organic acids, particularly salicylic acid and salicylates, citric acid and succinic acid. *Percutaneous Penetration Enhancers*, eds. Smith et al. (CRC Press, 1995) provides an excellent overview of the field and further background information on a number of chemical and physical enhancers.

Although many chemical permeation enhancers are known, there is an ongoing need for enhancers that are highly effective in increasing the rate at which a drug permeates the skin, do not result in skin damage, irritation, sensitization, or the like, and also allows neutralization of phenylpropanolamine hydrochloride during, rather than prior to, patch manufacture. It has now been discovered that hydroxide-releasing agents are highly effective permeation enhancers, even when used without co-enhancers, providing all of the aforementioned advantages relative to known permeation enhancers. Furthermore, in contrast to conventional enhancers, transdermal administration of drugs with hydroxide-releasing agents as permeation enhancers, employed at the appropriate levels, does not result in systemic toxicity.

SUMMARY OF THE INVENTION

It is thus a primary object of the invention to address the above-described need in the art by providing drug delivery systems, pharmaceutical formulations and methods for the transdermal administration of racemic phenylpropanolamine in neutral, uncharged form.

It is another object of the invention to provide a method for treating conditions, disorders or diseases that are responsive to administration of phenylpropanolamine by transdermally administering racemic phenylpropanolamine to a patient in need of such therapy.

It is still another object of the invention to provide a method for administering racemic phenylpropanolamine transdermally at a flux that is therapeutically effective for use as anorectic agent, a decongestant, an anxiolytic agent, or to decrease fatigue or confusion.

It is yet another object of the invention to provide a transdermal drug delivery system for administration of racemic phenylpropanolamine such that a therapeutically effective skin flux is achieved.

It is a further object of the invention to provide a chemical composition containing racemic phenylpropanolamine, formulated for transdermal drug delivery.

It is still a further object of the invention to provide a method for manufacturing a transdermal drug delivery system wherein phenylpropanolamine hydrochloride is converted to phenylpropanolamine base during system manufacture.

It is yet a further object of the invention to provide a method for administering racemic phenylpropanolamine transdermally in combination with a basic permeation enhancer.

Additional objects, advantages and novel features of the invention will be set forth in part in the description which follows, and in part will become apparent to those skilled in the art upon examination of the following, or may be learned by practice of the invention.

In one aspect of the invention, then, a method is provided for treating an individual suffering from a condition, disease or disorder that is responsive to administration of phenylpropanolamine, by transdermally administering a therapeutically effective amount of racemic phenylpropanolamine. The method is premised on the discovery that racemic phenylpropanolamine may in fact be administered through the skin or mucosal tissue at a therapeutically effective rate to achieve desired systemic effects, when a permeation enhancer, particularly a basic permeation enhancer, is coadministered with the drug.

In another aspect of the invention, a pharmaceutical composition and a transdermal therapeutic system are provided for transdermal administration of racemic phenylpropanolamine. The pharmaceutical composition contains racemic phenylpropanolamine, and is formulated for transdermal drug delivery. The transdermal drug delivery system is a laminated composite comprising a backing layer, a drug reservoir, and a means for affixing the composite to the skin. The drug reservoir and the affixing means may be distinct, such that a separate contact adhesive layer is provided which serves as the basal surface of the device, or the drug reservoir may itself be comprised of an adhesive layer which is suitable for contacting and adhering to the skin. Such therapeutic systems are in the nature of "solid matrix" type transdermal patches. Alternative systems, containing the drug in a liquid, gel or foam reservoir, may, however, be used as well.

In another aspect of the invention, a method is provided for increasing the rate at which phenylpropanolamine permeates through the body surface of a patient. The method involves administering the drug to a predetermined area of the patient's body surface in combination with a hydroxide-releasing agent in a predetermined amount effective to enhance the flux of the agent through the body surface without causing damage thereto. The predetermined amount of the hydroxide-releasing enhancer is preferably an amount effective to provide a pH at the body surface in the range of about 8.0 to 13, preferably about 8.0 to 11.5, more preferably about 8.5 to 11.5, during drug administration. If a skin patch is used, this is the preferred pH at the interface between the basal surface of the patch (i.e., the skin-contacting or mucosa-contacting surface of the patch) and the body surface. The optimal amount (or concentration) of any one hydroxide-releasing agent will, however, depend on the specific hydroxide-releasing agent, i.e., on the strength or weakness of the base, its molecular weight, and other factors as will be appreciated by those of ordinary skill in the art of transdermal drug delivery. This optimal amount may be determined using routine experimentation to ensure that the pH at the body surface is within the aforementioned ranges, i.e., in the range of about 8.0 to 13, preferably about 8.0 to 11.5, more preferably about 8.5 to 11.5. A conventional transdermal drug delivery device or "patch" may be used to administer the active agent, in which case the drug and hydroxide-releasing agent are generally present in a drug reservoir or reservoirs. However, the drug and hydroxide-releasing agent may also be administered to the body surface using a liquid or semisolid formulation. Alternatively, or in addition, the body surface may be pretreated with the enhancer, e.g., treated with a dilute solution of the hydroxide-releasing agent prior to transdermal drug administration. Such a solution will generally be comprised of a protic solvent (e.g., water or alcohol) and have a pH in the range of about 8.0 to 13, preferably about 8.0 to 11.5, more preferably about 8.5 to 11.5.

In a related aspect of the invention, a composition of matter is provided for delivering phenylpropanolamine through a body surface using a hydroxide-releasing agent as a permeation enhancer. Generally, the formulation comprises (a) a therapeutically effective amount of a drug, (b) a hydroxide-releasing agent in an amount effective to enhance the flux of the drug through the body surface without causing damage thereto, and (c) a pharmaceutically acceptable carrier suitable for topical or transdermal drug administration. The composition may be in any form suitable for application to the body surface, and may comprise, for example, a cream, lotion, solution, gel, ointment, paste or the like, and/or may be prepared so as to contain liposomes, micelles, and/or microspheres. The composition may be directly applied to the body surface or may involve use of a drug delivery device. In either case, it is preferred although not essential that water be present in order for the hydroxide-releasing agent to generate hydroxide ions and thus enhance the flux of the active agent through the patient's body surface. Thus, a formulation or drug reservoir may be aqueous, i.e., contain water, or may be nonaqueous and used in combination with an occlusive overlayer so that moisture evaporating from the body surface is maintained within the formulation or transdermal system during drug administration. In some cases, however, e.g., with an occlusive gel, a nonaqueous formulation may be used with or without an occlusive layer.

In another aspect of the invention, a drug delivery system is provided for the topical or transdermal administration of a drug using a hydroxide-releasing agent as a permeation enhancer. The system will generally comprise: at least one drug reservoir containing the drug and the hydroxide-releasing agent in an amount effective to enhance the flux of the drug through the body surface without causing damage thereto; a means for maintaining the system in drug and enhancer transmitting relationship to the body surface; and a backing layer that serves as the outer surface of the device during use. The backing layer may be occlusive or nonocclusive, although it is preferably occlusive. The drug reservoir may be comprised of a polymeric adhesive, which may serve as the basal surface of the system during use and thus function as the means for maintaining the system in drug and enhancer transmitting relationship to the body surface. The drug reservoir may also be comprised of a hydrogel, or it may be a sealed pouch within a "patch"-type structure wherein the drug and hydroxide-releasing agent are present in the pouch as a liquid or semi-solid formulation.

DETAILED DESCRIPTION OF THE INVENTION

Definitions and Overview

Figure 1:
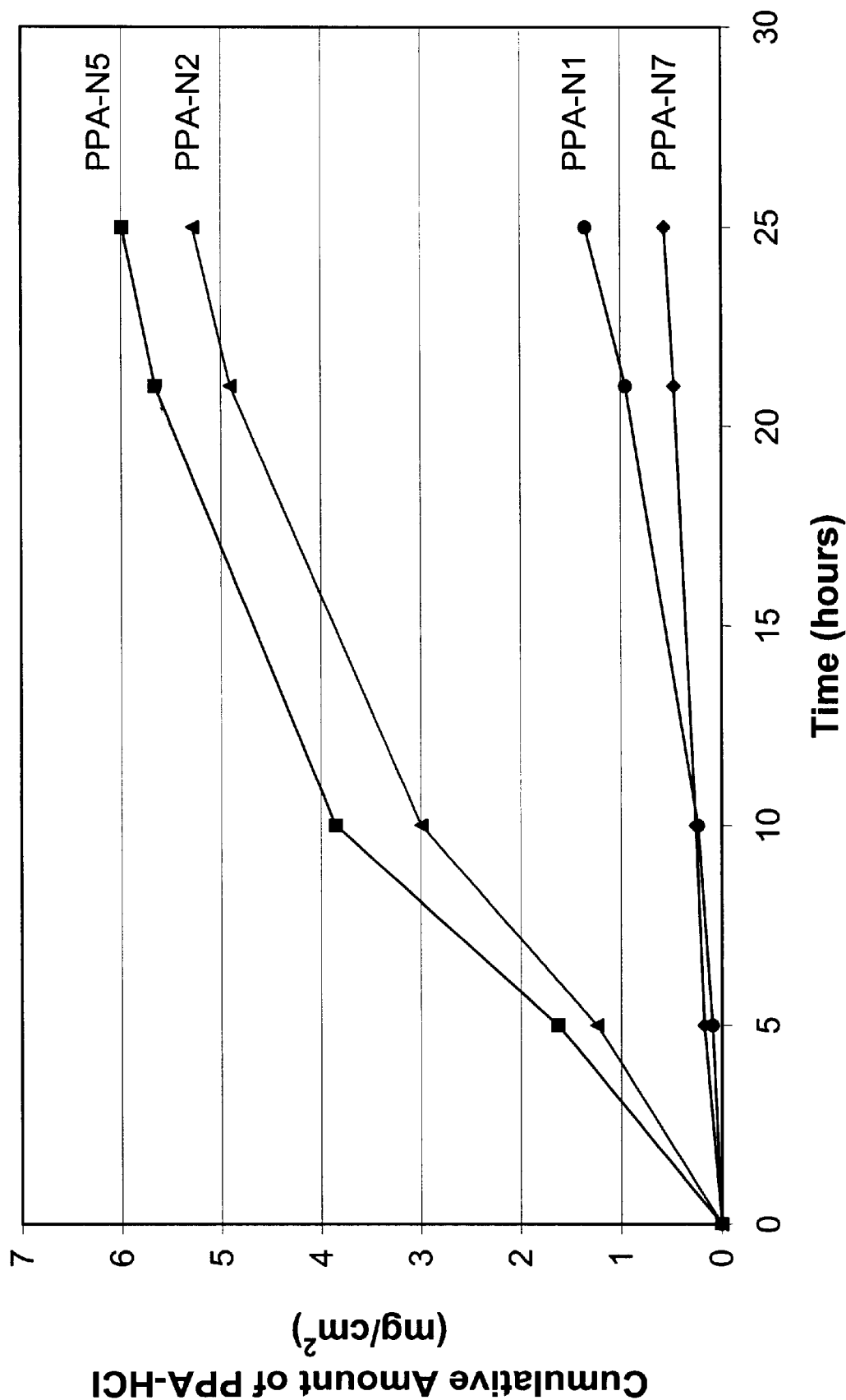
FIG. 1 is a graph illustrating the cumulative amount of racemic phenylpropanolamine permeated from matrix patches as described in Example 1.

Before describing the present invention in detail, it is to be understood that this invention is not limited to specific drug delivery systems, device structures, enhancers or carriers, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a pharmacologically active agent" includes a mixture of two or more active agents, reference to "an enhancer" includes mixtures of two or more enhancers, and the like.

In describing and claiming the present invention, the following terminology will be used in accordance with the definitions set out below.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method of "treating" a patient, as the term is used herein, thus encompasses both prevention of a disorder in a predisposed individual and treatment of the disorder in a clinically symptomatic individual.

The term "hydroxide-releasing agent" as used herein is intended to mean an agent that releases free hydroxide ions in an aqueous environment. The agent may contain hydroxide ions and thus release the ions directly (e.g., an alkali metal hydroxide), or the agent may be one that is acted upon chemically in an aqueous environment to generate hydroxide ions (e.g., a metal carbonate).

The terms "active agent," "drug" and "pharmacologically active agent" are used interchangeably herein to refer to a chemical material or compound that induces a desired effect, and include agents that are therapeutically effective, prophylactically effective, or cosmetically effective. Also included are derivatives and analogs of those compounds or classes of compounds specifically mentioned which also induce the desired effect. The primary active agent herein is racemic phenylpropanolamine.

"By therapeutically effective" amount is meant a nontoxic but sufficient amount of an active agent to provide the desired therapeutic effect.

By "transdermal" drug delivery is meant administration of a drug to the skin surface of an individual so that the drug passes through the skin tissue and into the individual's blood stream, thereby producing a systemic effect. The term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream.

The term "topical administration" is used in its conventional sense to mean delivery of a topical drug of a pharmacologically active agent to the skin or mucosa, as in, for example, the treatment of various skin disorders. Topical drug administration, in contrast to transdermal administration, provides a local rather than a systemic effect. Unless otherwise stated or implied, the terms "topical drug administration" and "transdermal drug administration" are used interchangeably.

The term "body surface" is used to refer to skin or mucosal tissue.

By "predetermined area" of skin or mucosal tissue, which refers to the area of skin or mucosal tissue through which PPA is delivered, is intended a defined area of intact unbroken living skin or mucosal tissue. That area will usually be in the range of about 5 cm$^2$ to about 200 cm$^2$, more usually in the range of about 5 cm$^2$ to about 100 cm$^2$, preferably in the range of about 20 cm$^2$ to about 60 cm$^2$. However, it will be appreciated by those skilled in the art of drug delivery that the area of skin or mucosal tissue through which the drug is administered may vary significantly, depending on patch configuration, dose, and the like.

"Penetration enhancement" or "permeation enhancement" as used herein relates to an increase in the permeability of the skin or mucosal tissue to the selected pharmacologically active agent, i.e., so that the rate at which the agent permeates therethrough (i.e., the "flux" of the agent through the body surface) is increased relative to the rate that would be obtained in the absence of permeation enhancement. The enhanced permeation effected through the use of such enhancers can be observed by measuring the rate of diffusion of drug through animal or human skin using, for example, a Franz diffusion apparatus as known in the art and as employed in the Examples herein.

An "effective" amount of a permeation enhancer is meant a nontoxic, nondamaging but sufficient amount of the enhancer to provide the desired increase in skin permeability and, correspondingly, the desired depth of penetration, rate of administration, and amount of drug delivered.

"Carriers" or "vehicles" as used herein refer to carrier materials suitable for transdermal drug administration. Carriers and vehicles useful herein include any such materials known in the art which is nontoxic and does not interact with other components of the composition in a deleterious manner.

The term "aqueous" refers to a formulation or drug delivery system that contains water or that becomes water-containing following application to the skin or mucosal tissue.

The term "racemic phenylpropanolamine" as used herein refers to a mixture of two or more of the four isomers of phenylpropanolamine, i.e., (+)-norephedrine, (−)-norephedrine, (+)-norpseudoephedrine, and (−)-norpseudoephedrine. Generally, however, the term refers to (±)-phenylpropanolamine, i.e., a racemic mixture of (−)-norephedrine and (+)-norephedrine. Phenylpropanolamine is generally although not necessarily administered in uncharged (electronically neutral) form, wherein the amine group of the molecule exists in free base form, i.e., as an —NH$_2$ moiety.

Accordingly, the invention pertains to a method, composition and drug delivery system for increasing the rate at which an active agent, e.g., racemic phenylpropanolamine, permeates through the body surface of a patient at a rate that is effective to result in therapeutically effective blood levels. The method involves administering the agent to a predetermined area of the patient's body surface in combination with a hydroxide-releasing agent in an amount effective to enhance the flux of the agent through the body surface without causing damage thereto.

Thus, the present method of transdermally delivering phenylpropanolamine may vary, but necessarily involves application of a composition containing racermic phenylpropanolamine to a predetermined area of the skin or mucosal tissue for a period of time sufficient to provide an effective blood level of drug for a desired period of time. The method may involve direct application of the composition as an ointment, gel, cream, or the like, or may involve use of a drug delivery device as taught in the art, e.g., in commonly assigned U.S. Pat. Nos. 4,915,950, 4,906,463, 5,091,186 or 5,246,705, or as described below.

The Permeation Enhancer

It will generally be necessary to administer racemic phenylpropanolamrine in conjunction with a permeation enhancer, in order to achieve a therapeutically effective flux through the skin.

Preferred permeation enhancers are basic compounds, with hydroxide-releasing agents particularly preferred. Hydroxide-releasing agents are described, for example, in co-pending, commonly assigned U.S. Ser. No. 09/569,889, filed May 11, 2000, for "Hydroxide-Releasing Agents as Skin Permeation Enhancers." A "hydroxide-releasing agent"

is a chemical compound that releases free hydroxide ions in the presence of an aqueous fluid. Therefore, any patch that is used should have an occlusive backing, or contain water, or both. Similarly, any topical formulation that is used should be aqueous or used in conjunction with an overlayer of an occlusive material.

The "hydroxide-releasing agent" is a chemical compound that releases free hydroxide ions in the presence of an aqueous fluid. The aqueous fluid may be natural moisture at the skin surface, or a patch or composition that is used may contain added water, and/or be used in connection with an occlusive backing. Similarly, any liquid or semisolid formulation that is used is preferably aqueous or used in conjunction with an overlayer of an occlusive material.

Any hydroxide-releasing agent may be used provided that the compound releases free hydroxide ions in the presence of an aqueous fluid. Examples of suitable hydroxide-releasing agents include, but are not limited to, inorganic hydroxides, inorganic oxides, and alkali metal or alkaline earth metal salts of weak acids. Inorganic hydroxides include, for example, ammonium hydroxide, alkali metal hydroxide and alkaline earth metal hydroxides, such as sodium hydroxide, calcium hydroxide, potassium hydroxide, magnesium hydroxide, and the like. Inorganic oxides include, for example, magnesium oxide, calcium oxide, and the like. Metal salts of weak acids include, for example, sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic), ammonium phosphate (dibasic), and the like. Preferred hydroxide-releasing agents are metal hydroxides such as sodium hydroxide and potassium hydroxide.

It is important that the amount of hydroxide-releasing agent in any patch or formulation is optimized so as to increase the flux of the drug through the body surface while minimizing any possibility of skin damage. In general, this means that the pH at the body surface in contact with a formulation or drug delivery system of the invention (i.e., the interface between the body surface and the formulation or delivery system) should be in the range of approximately 8.0 to 13, preferably about 8.0 to 11.5, more preferably about 8.5 to 11.5. This will typically although not necessarily mean that the pH of the formulation or the drug composition contained within a delivery system will be in the range of approximately 8.0 to 13, preferably about 8.0 to 11.5, more preferably about 8.5 to 11.5.

For inorganic hydroxides, the amount of hydroxide-releasing agent will typically represent about 0.5 wt. % to 4.0 wt. %, preferably about 0.5 wt. % to 3.0 wt. %, more preferably about 0.75 wt. % to 2.0 wt. % and optimally about 1.0 wt. %, of a topically applied formulation or of a drug reservoir of a drug delivery system, or "patch." The aforementioned amount applies to formulations and patches in which the active agent is (1) an uncharged molecule, i.e., the phenylpropanolamine is in nonionized, free base form, and (2) there are no additional species in the formulation or patch that could react with or be neutralized by the inorganic hydroxide. For formulations and patches in which the phenylpropanolamine is in the form of an acid addition salt, and/or wherein there are additional species in the formulations or systems that can be neutralized by or react with the hydroxide-releasing agent (i.e., acidic inactive ingredients), the amount of inorganic hydroxide will be the total of (1) the amount necessary to neutralize the acid addition salt and/or other base-neutralizable species, plus (2) about 0.5 wt. % to 4.0 wt. %, preferably about 0.5 wt. % to 3.0 wt. %, more preferably about 0.75 wt. % to 2.0 wt. % and optimally about 1.0 wt. %, of the formulation or drug reservoir. That is, for an acid addition salt of phenylpropanolamine, the inorganic hydroxide should be present in an amount just sufficient to neutralize the salt, plus an additional amount (i.e., about 0.5 wt. % to 4.0 wt. %, preferably about 0.5 wt. % to 3.0 wt. %, more preferably about 0.75 wt. % to 2.0 wt. % and optimally about 1.0 wt. %) to enhance the flux of the drug through the skin or mucosal tissue. For patches, the aforementioned percentages are given relative to the total dry weight of the formulation components and the adhesive, gel or liquid reservoir.

For other hydroxide-releasing agents such as inorganic oxides and metal salts of weak acids, the amount of hydroxide-releasing agent in the formulation or drug delivery system may be substantially higher, as high as 20 wt. %, in some cases as high as 25 wt. % or higher, but will generally be in the range of approximately 2 wt. % to 20 wt. %.

Still greater amounts of hydroxide-releasing agent may be used by controlling the rate and/or quantity of release of the hydroxide-releasing agent preferably during the drug delivery period itself.

However, for all hydroxide-releasing agents herein, the optimum amount of any particular agent will depend on the strength or weakness of the base, the molecular weight of the base, and any other acidic species in the formulation or patch. One skilled in the art may readily determine the optimum amount for any particular hydroxide-releasing agent by ensuring that a formulation or drug delivery system should in all cases be effective to provide a pH at the skin surface in the range of about 8.0 to 13, preferably in the range of about 8.0 to 11.5, more preferably in the range of about 8.5 to 11.5, during application to reach the desired pH at the body surface. This in turn ensures that the degree of enhancement is optimized while the possibility of damage to the body surface,is eliminated or at least substantially minimized.

Other enhancers may be used as an alternative or in addition to the hydroxide-releasing agent. These enhancers include, for example, the following: sulfoxides such as dimethylsulfoxide (DMSO" and decylmethylsulfoxide ($C_{10}MSO$); ethers such as diethylene glycol monoethyl ether (available commercially as Transcutol®) and diethylene glycol monomethyl ether, surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); the 1-substituted azacycloheptan-2-ones, particularly 1-n-dodecylcyclazacycloheptan-2-one (available under the trademark Azone® from Nelson Research & Development Co., Irvine, Calif.; see U.S. Pat. Nos. 3,989,816, 4,316,893, 4,405,616 and 4,557,934); alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML, see, e.g., U.S. Pat. No. 4,568,343), amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine, terpenes; alkanones, and organic acids, particularly salicylic acid and salicylatles, citric acid and succinic acid. As noted earlier herein, *Percutaneous Penetration Enhancers,* eds. Smith et al. (CRC Press, 1995) provides an excellent overview of the field and further information concerning possible secondary enhancers for use in conjunction with the present invention.

It is preferred, however, that a hydroxide-releasing agent be used as the permeation enhancer without any other permeation enhancers.

In addition, it is preferred that the pH of the body surface in contact with a formulation or drug delivery system of the invention (i.e., the interface between the body surface and the formulation or delivery system) be in the range of approximately 8.0 to 13, preferably about 8.0 to 11.5, most preferably about 8.5 to 11.5. Similarly, it is preferred that the pH of the formulation or the drug composition contained within a delivery system be in the range of approximately 8.0 to 13, preferably about 8.0 to 11.5, most preferably about 8.5 to 11.5.

The Active Agent

The active agent administered is racemic phenylpropanolamine, i.e., a mixture of any two or more of the four isomers of phenylpropanolamine, which, as noted above, are (+)-norephedrine, (−)-norephedrine, (+)-norpseudoephedrine, and (−)-norpseudoephedrine. Normally, the active agent is (±)-phenylpropanolamine, i.e., a racemic mixture of (−)-norephedrine and (+)-norephedrine.

If desired, the racemic phenylpropanolamine can be co-administered with any of a number of other active agents. These additional active agents include the broad classes of compounds normally delivered through body surfaces and membranes, including skin. In general, this includes: analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antineoplastic agents; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; parasympatholytics; peptide drugs; psychostimulants; sedatives; steroids; sympathomimetics; tranquilizers; and vasodilators including general coronary, peripheral and cerebral.

Preferred classes of active agents for coadministration with phenylpropanolamine using the present systems and methods are, like phenylpropanolamine, anorectic agents and drugs commonly used in allergy and cold preparations. Specific examples of preferred active agents for co-administration with phenylpropanolamine include, but are not limited to, brompheniramine maleate, chlorpheniramine maleate, clemastine fumarate, acetaminophen, aspirin, guaifenesin, phenylephrine hydrochloride, and dextromethorphan hydrobromide.

Formulations

The method of delivery of the racemic phenylpropanolamine may vary, but necessarily involves application of a formulation or drug delivery system containing a hydroxide-releasing agent to a predetermined area of the skin or other tissue for a period of time sufficient to provide the desired local or systemic effect. The method may involve direct, topical application of the composition as an ointment, gel, cream, or the like, or may involve use of a drug delivery device. In either case, water must be present in order for the hydroxide-releasing agent to generate hydroxide ions and thus enhance the flux of the active agent through the patient's body surface. Thus, a formulation or drug reservoir may be aqueous, i.e., contain water, or may be nonaqueous and used in combination with an occlusive overlayer so that moisture evaporating from the body surface is maintained within the formulation or transdermal system during drug administration. In some cases, however, e.g., with an occlusive gel, a nonaqueous formulation may be used with or without an occlusive layer.

Suitable formulations include ointments, creams, gels, lotions, pastes, and the like. Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in *Remington: The Science and Practice of Pharmacy,* 19th Ed. (Easton, Pa.: Mack Publishing Co., 1995), at pages 1399–1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, see *Remington: The Science and Practice of Pharmacy* for further information.

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions, as is known in the art, are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like.

Pastes are semisolid dosage forms in which the active agent is suspended in a suitable base. Depending on the nature of the base, pastes are divided between fatty pastes or those made from a single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having a lipid wall comprising a lipid bilayer, and can be used as drug delivery systems herein as well. Liposome preparations for use in the instant invention include cationic (positively charged), anionic (negatively charged) and neutral preparations. Cationic liposomes are readily available. For example, N[1-2,3-dioleyloxy)propyl]-N,N,N-triethylammonium (DOTMA) liposomes are available under the tradename Lipofectin® (GEBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10 and nonoxynol 30. Micelle formulations can be used in conjunction with the present invention either by incorporation into the reservoir of a topical or transdermal delivery system, or into a formulation to be applied to the body surface.

Microspheres, similarly, may be incorporated into the present formulations and drug delivery systems. Like liposomes and micelles, microspheres essentially encapsulate a drug or drug-containing formulation. They are generally although not necessarily formed from lipids, preferably charged lipids such as phospholipids. Preparation of lipidic microspheres is well known in the art and described in the pertinent texts and literature.

Various additives, known to those skilled in the art, may be included in the phenylpropanolamine compositions. For example, solvents, including relatively small amounts of alcohol, may be used to facilitate solubilization of the active agent. Other optional additives include opacifiers, antioxidants, fragrance, colorant, gelling agents, thickening agents, stabilizers, and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

The concentration of the active agent in the formulation can vary a great deal, and will depend on a variety of factors, including the disease or condition to be treated, the desired effect, the ability and speed of the active agent to reach its intended target, and other factors within the particular knowledge of the patient and physician. Preferred formulations will typically contain on the order of about 10 wt. % to 30 wt. % racemic phenylpropanolamine, optimally about 15 wt. % to 25 wt. % racemic phenylpropanolamine.

Transdermal Delivery Systems

An alternative and preferred method for administering racemic phenylpropanolamine transdermally involves the use of a drug delivery system, e.g., a topical or transdermal "patch," wherein the active agent is contained within a laminated structure that is to be affixed to the skin. In such a structure, the drug composition is contained in a layer, or "reservoir," underlying an upper backing layer. The laminated structure may contain a single reservoir, or it may contain multiple reservoirs.

In one embodiment, the reservoir comprises a polymeric matrix of a pharmaceutically acceptable adhesive material that serves to affix the system to the skin during drug delivery; typically, the adhesive material is a pressure-sensitive adhesive (PSA) that is suitable for long-term skin contact, and which should be physically and chemically compatible with the active agent, hydroxide-releasing agent, and any carriers, vehicles or other additives that are present. Examples of suitable adhesive materials include, but are not limited to, the following: polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene). Preferred adhesives are polyisobutylenes.

The backing layer functions as the primary structural element of the transdermal system and provides the device with flexibility an, preferably, occlusivity. The material used for the backing layer should be inert and incapable of absorbing drug, hydroxide-releasing agent or components of the formulation contained within the device. The backing is preferably comprised of a flexible elastomeric material that serves as a protective covering to prevent loss of drug and/or vehicle via transmission through the upper surface of the patch, and will preferably impart a degree of occlusivity to the system, such that the area of the body surface covered by the patch becomes hydrated during use. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. The materials used as the backing layer are either occlusive or permeable, as noted above, although occlusive backings are preferred, and are generally derived from synthetic polymers (e.g., polyester, polyethylene, polypropylene, polyurethane, polyvinylidine chloride, and polyether amide), natural polymers (e.g., cellulosic materials), or macroporous woven and nonwoven materials.

During storage and prior to use, the laminated structure includes a release liner. Immediately prior to use, this layer is removed from the device so that the system may be affixed to the skin. The release liner should be made from a drug/vehicle impermeable material, and is a disposable element which serves only to protect the device prior to application. Typically, the release liner is formed from a material impermeable to the pharmacologically active agent and the hydroxide-releasing agent, and which is easily stripped from the transdermal patch prior to use.

In an alternative embodiment, the drug-containing reservoir and skin contact adhesive are present as separate and distinct layers, with the adhesive underlying the reservoir. In such a case, the reservoir may be a polymeric matrix as described above. Alternatively, the reservoir may be comprised of a liquid or semisolid formulation contained in a closed compartment or "pouch," or is may be a hydrogel reservoir, or may take some other form. Hydrogel reservoirs are particularly preferred herein. As will be appreciated by those skilled in the art, hydrogels are macromolecular networks that absorb water and thus swell but do not dissolve in water. That is, hydrogels contain hydrophilic functional groups that provide for water absorption, but the hydrogels are comprised of crosslinked polymers that give rise to aqueous insolubility. Generally, then, hydrogels are comprised of crosslinked hydrophilic polymers such as a polyurethane, a polyvinyl alcohol, a polyacrylic acid, a polyoxyethylene, a polyvinylpyrrolidone, a poly (hydroxyethyl methacrylate) (poly(HEMA)), or a copolymer or mixture thereof Particularly preferred hydrophilic polymers are copolymers of HEMA and polyvinylpyrrolidone.

Additional layers, e.g., intermediate fabric layers and/or rate-controlling membranes, may also be present in any of these drug delivery systems. Fabric layers may be used to facilitate fabrication of the device, while a rate-controlling membrane may be used to control the rate at which a component permeates out of the device. The component may be a drug, a hydroxide-releasing agent, an additional enhancer, or some other component contained in the drug delivery system.

A rate-controlling membrane, if present, will be included in the system on the skin side of one or more of the drug reservoirs. The materials used to form such a membrane are selected to limit the flux of one or more components contained in the drug formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like.

Generally, the underlying surface of the transdermal device, i.e., the skin contact area, has an area in the range of about 5 $cm^2$ to 200 $cm^2$, preferably 5 $cm^2$ to 100 $cm^2$, more preferably 20 $cm^2$ to 60 $cm^2$. That area will vary, of course, with the amount of the drug to be delivered and the flux of the drug through the body surface. Larger patches will be necessary to accommodate larger quantities of drug, while smaller patches can be used for small quantities of drug and/or drugs that exhibit a relatively high permeation rate.

Such drug delivery systems may be fabricated using conventional coating and laminating techniques known in the art. For example adhesive matrix systems can be prepared by casting a fluid admixture adhesive, drug and vehicle onto the backing layer followed by lamination of the release liner. Similarly the adhesive mixture may be cast onto the release liner, followed by lamination of the release liner. Alternatively, the drug reservoir may be prepared in the absence of drug or excipient, and then loaded by "soaking" in a drug/vehicle mixture. In general, transdermal systems of the invention are fabricated by solvent evaporation, film casting, melt extrusion, thin film lamination, die cutting, or the like. The hydroxide-releasing agent will generally be incorporated into the device during patch manufacture rather than subsequent to preparation of the device. For active agents that are obtained in salt form, an enhancer that doubles as a neutralizing agent is incorporated into the device during patch manufacture rather than subsequent to preparation of the device. Thus, for acid addition salts of PPA, e.g., the hydrochloride salt of racemic phenylpropanolamine, a basic enhancer such as a hydroxide-releasing agent will neutralize the drug during manufacture of the transdermal system, resulting in a final drug delivery device in which the drug is present in nonionized, neutral form, preferably along with an excess of the basic compound to serve as a permeation enhancer.

In a preferred delivery system, an adhesive overlayer that also serves as a backing for the delivery system is used to better secure the patch to the body surface. This overlayer is sized such that it extends beyond the drug reservoir so that adhesive on the overlayer comes into contact with the body surface. The overlayer is useful because the adhesive/drug reservoir layer may lose its adhesion a few hours after application due to hydration. By incorporating such an adhesive overlayer, the delivery system remains in place for the required period of time.

Other types and configurations of transdermal drug delivery systems may also be used in conjunction with the method of the present invention, i.e., the use of a hydroxide-releasing agent as a permeation enhancer, as will be appreciated by those skilled in the art of transdermal drug delivery. See, for example, Ghosh, *Transdermal and Topical Drug Delivery Systems* (Interpharm Press, 1997), particularly Chapters 2 and 8.

As with the formulations of the invention discussed in the preceding section, the composition containing the racemic phenylpropanolamine within the drug reservoir(s) of these laminated system may contain a number of components. In some cases, the drug and hydroxide-releasing agent may be delivered "neat," i.e., in the absence of additional liquid. In most cases, however, the drug will be dissolved, dispersed or suspended in a suitable pharmaceutically acceptable vehicle, typically a solvent or gel. Other components which may be present include preservatives, stabilizers, surfactants, and the like.

Utility and Administration

The formulations and delivery systems of the invention are useful for transdermal administration of racemic phenylpropanolamine to treat any condition, disease or disorder that is responsive to administration of phenylpropanolamine. Typically, the formulations and delivery systems of the invention are used to administer phenylpropanolamine as an anorectic agent (i.e., for appetite suppression), as a decongestant, as an anxiolytic agent, or to decrease fatigue and confusion. Most commonly, the drug is used as either an anorectic agent or a decongestant.

The daily dosage administered will, of course, vary from subject to subject and depend on the particular disorder or condition, the severity of the symptoms, the subject's age, weight and general condition, and the judgment of the prescribing physician. Other factors specific to transdermal drug delivery include the solubility and permeability of the carrier and adhesive layer in a drug delivery system, if one is used, and the period of time for which such a device will be affixed to the skin or other body surface. Generally, however, a daily dosage of racemic phenylpropanolamine using the present formulations and delivery systems will be in the range of about 10 mg/day to about 250 mg/day, preferably about 25 mg/day to about 200 mg/day.

The invention accordingly provides a novel and highly effective means for administering racemic phenylpropanolamine through the body surface (skin or mucosal tissue) of a human or animal. Surprisingly, the increase in permeation achieved by co-administration of a basic enhancer is not accompanied by any noticeable tissue damage, irritation, or sensitization. The invention thus represents an important advance in the field of transdermal drug delivery.

The practice of the present invention will employ, unless otherwise indicated, conventional techniques of drug formulation, particularly topical drug formulation, which are within the skill of the art. Such techniques are fully explained in the literature. See *Remington: The Science and Practice of Pharmacy*, cited supra, as well as Goodman & Gilman's *The Pharmacological Basis of Therapeutics*, 9th Ed. (New York: McGraw-Hill, 1996).

It is to be understood that while the invention has been described in conjunction with the preferred specific embodiments thereof, the foregoing description, as well as the examples which follow, are intended to illustrate and not limit the scope of the invention. Other aspects, advantages and modifications will be apparent to those skilled in the art to which the invention pertains. All patents, patent applications, journal articles and other references cited herein are incorporated by reference in their entireties.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C and pressure is at or near atmospheric.

EXAMPLE 1

An in vitro skin permeation study was conducted using four phenylpropanolamine hydrochloride (PPA-HCl) transdermal systems. The formulations used to prepare these systems are listed in Table 1, which includes weight and weight percent of each component in the formulations. The weight of sodium hydroxide was 0 g, 0.165 g, 0.195 g, and 0.23 g for formulation #PPA-N7,-N1, -N2, -and -N5, respectively. Each formulation was coated onto a release liner and dried in an oven at 55° C. for two hours to remove water and other solvents. The dried drug-in-adhesive/release liner film was laminated to a backing film. The backing/drug-in-adhesive/release liner laminate was then cut into round discs with a diameter of $11/16$ inch. The theoretical percent weight for each component after drying (calculated assuming all the volatile ingredients were completely removed during drying) is listed in Table 2.

The in vitro permeation of PPA-HCl through human cadaver skin from these discs was performed using Franz-type diffusion cells with a diffusion area of 1 $cm^2$. The volume of receiver solution was 8 ml. Human cadaver skin was cut to the desired size and placed on a flat surface with the stratum corneum side facing up. The release liner was peeled away from the disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Three diffusion cells were used for each formulation.

The cells were filled with DI water. The receiver solution was completely withdrawn and replaced with fresh DI water at each time point. The samples taken were analyzed by an HPLC for the concentration of PPA-HCl in the receiver solution. The cumulative amount of PPA-HCl that permeated across the human cadaver skin was calculated using the measured PPA-HCl concentrations in the receiver solutions, which were plotted versus time and shown in FIG. 1.

Since PPA-HCl is an acid addition salt of a free base, it reacts with NaOH. The concentration of NaOH in the system after the reaction is completed depends on the amount of PPA-HCl added. The remaining NaOH concentration after the reaction is completed is defined as "excess NaOH concentration," calculated as explained in the foregoing example. The excess NaOH concentration for four PPA-HCl systems, #PPA-N7, -N1, -N2, -and -N5, were calculated and listed in Table 3.

The pH of the patch was measured using the following procedures. A 2.5 $cm^2$ circular patch was punched out. Ten ml purified water was pipetted into a glass vial, and a stir bar was added; the liner was removed from the patch and placed in the vial along with the patch. The vial was then placed on a stir plate and the water/patchAiner mixture was stirred for 5 minutes, at which point the liner was removed from the vial and discarded. The vial was again placed on a stir plate and stirring continued for an additional 18 hours. After 18 hours, the stir bar was removed from the vial and the pH of the solution determined using a calibrated pH meter. The measured pHs for the PPA-HCl transdermal systems are listed in Table 3.

TABLE 1

Weight and Weight Percent of Each Component (Based on Total Solution Weight) for Four PPA-HCl Transdermal Systems

|  | PPA-N7 | PPA-N1 | PPA-N2 | PPA-N5 |
| --- | --- | --- | --- | --- |
| PPA-HCl | 0.75 g (8.5%) | 0.75 g (8.2%) | 0.75 g (8.1%) | 0.75 g (8.1%) |
| NaOH | 0 | 0.165 g (1.8%) | 0.195 g (2.1%) | 0.23 g (2.5%) |
| DI water | 1.1 g (12.4%) | 1.265 g (13.8%) | 1.295 g (14.0%) | 1.33 g (14.3%) |
| Propylene glycol | 0.5 g (5.6%) | 0.5 g (5.4%) | 0.5 g (5.4%) | 0.5 g (5.4%) |
| Methylal | 1 g (11.3%) | 1 g (10.9%) | 1 g (10.8%) | 1 g (10.7%) |
| Heptane | 1.5 g (16.9%) | 1.5 g (16.3%) | 1.5 g (16.2%) | 1.5 g (16.1%) |
| PIB adhesive (30% solid) | 4 g (45.2%) | 4 g (43.6%) | 4 g (43.3%) | 4 g (43.0%) |

TABLE 2

Weight and Theoretical Weight Percent of Each Component in the Dried Film for Four PPA-HCl Transdermal Systems

|  | PPA-N7 | PPA-N1 | PPA-N2 | PPA-N5 |
| --- | --- | --- | --- | --- |
| PPA-HCl | 0.75 g (30.6%) | 0.75 g (28.7%) | 0.75 g (28.4%) | 0.75 g (28.0%) |
| NaOH | 0 | 0.165 g (6.3%) | 0.195 g (7.4%) | 0.23 g (8.6%) |
| PIB adhesive | 1.2 g (49.0%) | 1.2 g (45.9%) | 1.2 g (45.4%) | 1.2 g (44.8%) |
| Propylene glycol | 0.5 g (20.4%) | 0.5 g (19.1%) | 0.5 g (18.9%) | 0.5 g (18.7%) |

TABLE 3

Excess NaOH Concentration and pH of Four PPA-HCl Transdermal Systems

|  | PPA-N7 | PPA-N1 | PPA-N2 | PPA-N5 |
| --- | --- | --- | --- | --- |
| Excess NaOH Concentration (wt. %) |  | 0.20% | 1.33% | 2.62% |
| pH | 7.33 | 10.08 | 10.16 | 10.88 |

Even though patch #PPA-N1 contained 6.3% NaOH (Table 2), the cumulative amount of PPA-HCl that permeated across the human cadaver skin at 24 hours from this formulation (1.35 mg/cm$^2$, FIG. 1) was only slightly higher than that from the formulation without NaOH (PPA-N7, 0.56 mg/cm$^2$). This may be due to the consumption of NaOH by the reaction between NaOH and PPA-HCl, which reduced the NaOH concentration to only 0.20% as the excess NaOH concentration shown in Table 3. This result indicated that the permeation of PPA-HCl could be enhanced with an excess NaOH concentration as low as 0.20%.

The cumulative amount of PPA-HCl across human cadaver skin at 24 hours increased from 1.35 mg/cm$^2$ to 5.99 mg/cm$^2$ when the calculated excess NaOH concentration in the dried patch was increased from 0.20% to 2.62%. The cumulative amount of PPA-HCl across human cadaver skin at 24 hours from the formulation with an excess NaOH concentration of 1.33% (PPA-N2, 5.2 mg/cm$^2$) is about 5 times higher than that from the formulation with an excess NaOH concentration of 0.20% (PPA-N1, 1.35 mg/cm$^2$).

The pH of the PPA-HCl patch increased from 10.08 to 10.88 when the calculated excess NaOH concentration in the dried patch was increased from 0.20% to 2.62%. Skin irritation could be related to the pH of the patch, which depends on the excess NaOH concentration.

EXAMPLE 2

Figure 2:
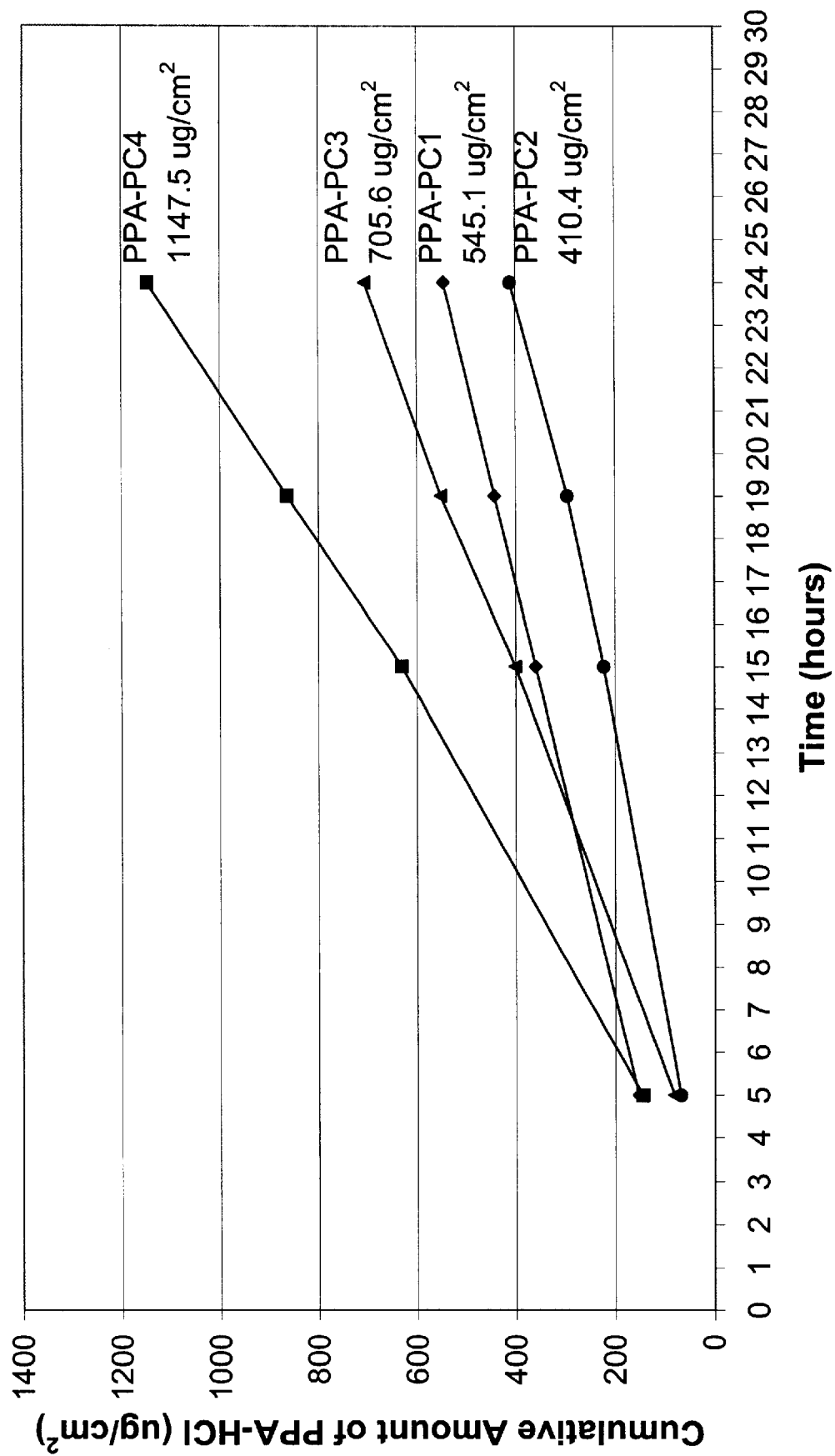
FIG. 2 is a graph illustrating the cumulative amount of racemic phenylpropanolamine permeated from matrix patches as described in Example 2.

An in vitro skin permeation study was conducted using four phenylpropanolamine hydrochloride (PPA-HCl) transdermal systems. The formulations used to prepare these systems are listed in Table 4, which includes weight and weight percent of each component in the formulations. The weight of sodium carbonate (Na$_2$CO$_3$) was 0 g, 0.29 g, 0.44 g, and 0.74 g for formulations #PPA-PC1, -PC2, -PC3, and -PC4 respectively. The matrix patches were prepared and evaluated using the same procedures as set forth in Example 1. The theoretical percent weight for each ingredient after drying (calculated assuming all the volatile ingredients were completely removed during drying) is listed in Table 5. The cumulative amount of PPA-HCl across human cadaver skin was calculated using the measured PPA-HCl concentrations in the receiver solutions, which are shown in Table 6 and FIG. 2.

Since PPA-HCl is a salt of a free base, it reacts with Na$_2$CO$_3$. The concentration of Na$_2$CO$_3$ in the system after the reaction is completed depends on the amount of PPA-HCl added. The remaining sodium carbonate concentration after the reaction is completed is defined as "excess Na$_2$CO$_3$ concentration," which is calculated by the following equation.

$$[Na_2CO_{3\ excess}] = [Na_2CO_{3\ total}] - [Na_2CO_{3\ needed\ for\ neutralization}]$$

The excess Na$_2$CO$_3$ concentration for four PPA-HCl systems, #PPA-PC 1, -PC2, -PC3 and -PC4 were calculated and listed in Table 7.

The pH of the patch was determined using the procedure of example 1 and the results are listed in Table 7.

TABLE 4

Weight and Weight Percent of Each Component (Based on Total Solution Weight) for Four PPA-HCl Transdermal Systems

|  | PPA-PC1 | PPA-PC2 | PPA-PC3 | PPA-PC4 |
|---|---|---|---|---|
| PPA-HCl | 0.5 g (6.7%) | 0.5 g (5.7%) | 0.5 g (5.6%) | 0.5 g (5.5%) |
| $Na_2CO_3$ | 0 | 0.29 g (3.3%) | 0.44 g (5.0%) | 0.74 g (8.1%) |
| DI water | 1.0 g (13.5%) | 2.0 g (23.0%) | 2.0 g (22.6%) | 2.0 g (21.9%) |
| Methyl alcohol | 0.5 g (6.7%) | 0.5 g (5.7%) | 0.5 g (5.6%) | 0.5 g (5.5%) |
| Propylene glycol | 0.2 g (2.7%) | 0.2 g (2.3%) | 0.2 g (2.3%) | 0.2 g (2.2%) |
| HPMC | 0.01 g (0.1%) | 0.01 g (0.1%) | 0.01 g (0.1%) | 0.01 g (0.1%) |
| Heptane | 1.2 g (16.2%) | 1.2 g (13.8%) | 1.2 g (13.6%) | 1.2 g (13.1%) |
| PIB adhesive (30% solid) | 4 g (54.0%) | 4 g (46.0%) | 4 g (45.2%) | 4 g (45.2%) |

TABLE 5

Weight and Theoretical Weight Percent of Each Component in the Dried Film for Four PPA-HCl Transdermal Systems

|  | PPA-PC1 | PPA-PC2 | PPA-PC3 | PPA-PC4 |
|---|---|---|---|---|
| PPA-HCl | 0.5 g (26.2%) | 0.5 g (22.7%) | 0.5 g (21.3%) | 0.5 g (18.9%) |
| $Na_2CO_3$ | 0 | 0.29 g (13.2%) | 0.44 g (18.7%) | 0.74 g (27.9%) |
| Propylene glycol | 0.2 g (10.5%) | 0.2 g (9.1%) | 0.2 g (8.5%) | 0.2 g (7.5%) |
| HPMC | 0.01 g (0.5%) | 0.01 g (0.5%) | 0.01 g (0.4%) | 0.01 g (0.4%) |
| PIB adhesive | 1.2 g (62.8%) | 1.2 g (54.5%) | 1.2 g (51.1%) | 1.2 g (45.3%) |

TABLE 6

Cumulative Amount of PPA-HCl across human cadaver skin for PPA-HCl Transdermal Systems ($\mu g/cm^2$)

|  | PPA-PC1 | PPA-PC2 | PPA-PC3 | PPA-PC4 |
|---|---|---|---|---|
| 5 hours | 152.8 | 68.0 | 81.1 | 144.8 |
| 15 hours | 359.5 | 222.7 | 400.8 | 631.2 |
| 19 hours | 442.7 | 295.7 | 551.5 | 864.3 |
| 24 hours | 545.1 | 410.4 | 705.6 | 1147.5 |

TABLE 7

Excess $Na_2CO_3$ Concentration and pH of Four PPA-HCl Transdermal Systems

|  | PPA-PC1 | PPA-PC2 | PPA-PC3 | PPA-PC4 |
|---|---|---|---|---|
| Excess $Na_2CO_3$ Concentration (wt. %) | — | 0.4% | 6.7% | 16.7% |
| pH | 6.54 | 9.81 | 9.86 | 10.17 |

Even though patch #PPA-PC2 contained 13.2% $Na_2CO_3$ (Table 5), the cumulative amount of PPA-HCl that permeated across the human cadaver skin at 24 hours (410.4 $\mu g/cm^2$, Table 6) was lower than that from the formulation without $Na_2CO_3$ (PPA-PC1, 545.1 $\mu g/cm^2$). This may be due to the consumption of $Na_2CO_3$ by the reaction between $Na_2CO_3$ and PPA-HCl, which reduced the $Na_2CO_3$ concentration to only 0.4% as the excess $Na_2CO_3$ concentration (Table 7).

When the calculated excess $Na_2CO_3$ concentration in the dried patch was further increased from 0.4% to 16.7%, the cumulative amount of PPA-HCl that permeated across the human cadaver skin at 24 hours was increased from 410.4 to 1147.5 $\mu g/cm^2$. This result indicated that the permeation of PPA-HCl could be enhanced by $Na_2CO_3$, even though the required excess $Na_2CO_3$ concentration is higher than that of NaOH. Greater amounts of $Na_2CO_3$ may be necessary because it is a weaker base compared to NaOH and the molecular weight of $Na_2CO_3$ is higher than that of NaOH.

The pH of the PPA-HCl patch measured using the procedures listed above increased from 9.81 to 10.17 when the calculated excess $Na_2CO_3$ concentration in the dried patch was increased from 0.4% to 16.7%.

EXAMPLE 3

Figure 3:
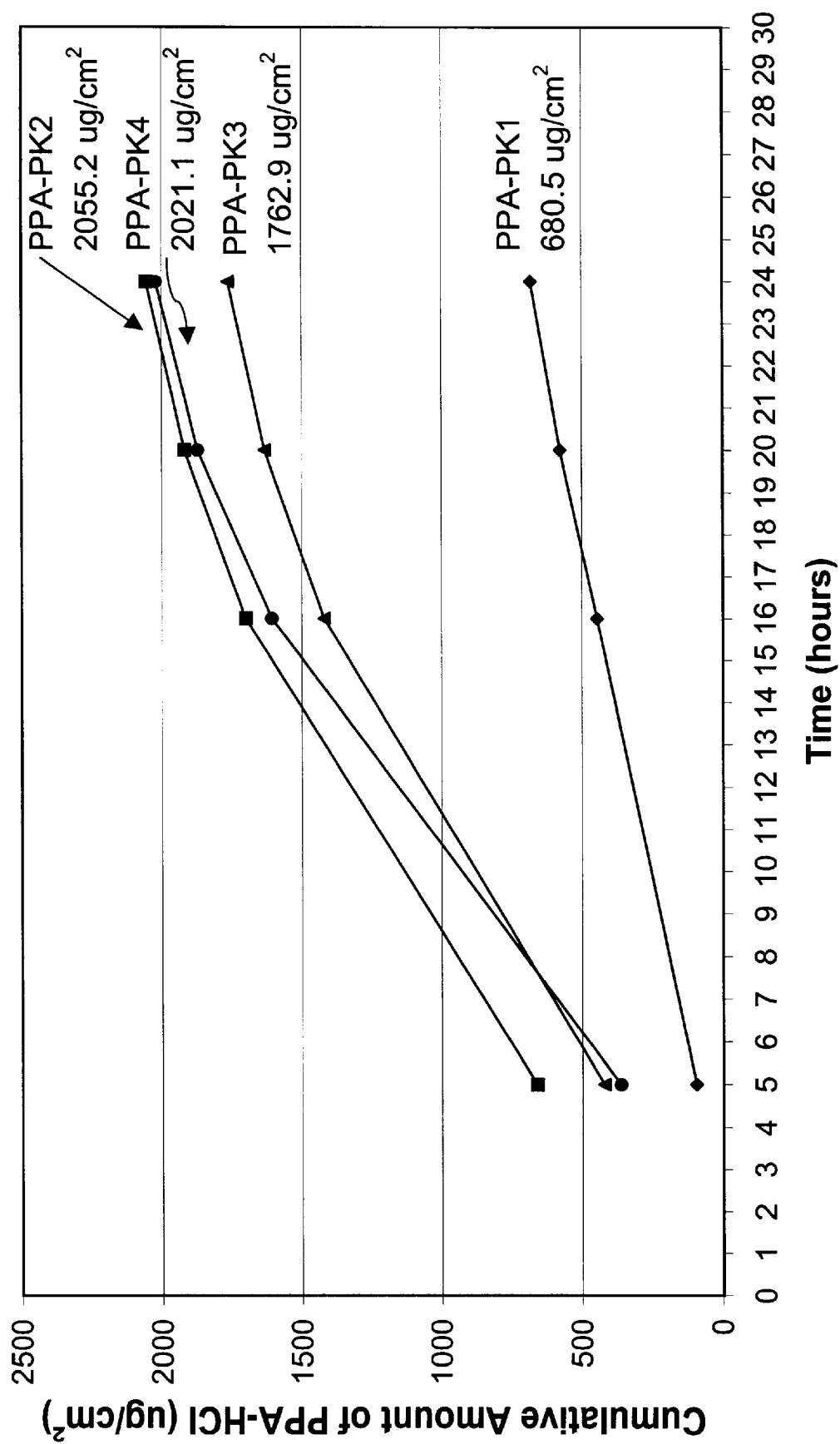
FIG. 3 is a graph illustrating the cumulative amount of racemic phenylpropanolamine permeated from matrix patches as described in Example 3.

An in vitro skin permeation study was conducted using four phenylpropanolamine hydrochloride (PPA-HCl) transdermal systems. The formulations used to prepare these systems are listed in Table 8, which includes weight and weight percent of each component in the formulations. The weight of potassium phosphate, tribasic ($K_3PO_4$) was 0 g, 0.57 g, 0.6 g, and 0.66 g for formulation #PPA-PK1, -PK2, -PK3, and -PK4 respectively. The matrix patches were prepared and evaluated using the same procedures as set forth in Example 1. The theoretical percent weight for each ingredient after drying (calculated assuming all the volatile ingredients were completely removed during drying) is listed in Table 9. The cumulative amount of PPA-HCl across human cadaver skin was calculated using the measured PPA-HCl concentrations in the receiver solutions, which were shown in Table 10 and FIG. 3.

Since PPA-HCl is a salt of a free base, it reacts with $K_3PO_4$. The concentration of $K_3PO_4$ in the system after the reaction is completed depends on the amount of PPA-HCl added. The remaining $K_3PO_4$ concentration after the reaction is completed is defined as "excess $K_3PO_4$ concentration," which is calculated by the following equation.

$$[K_3PO_{4\ excess}] = [K_3PO_{4\ total}] - [K_3PO_{4\ needed\ for\ neutralizaton}]$$

The excess $K_3PO_4$ concentration for four PPA-HCl systems, #PPA-PK1, -PK2, -PK3 and -PK4 were calculated and listed in Table 11.

TABLE 8

Weight and Weight Percent of Each Component (Based on Total Solution Weight) for Four PPA-HCl Transdermal Systems

|  | PPA-PK1 | PPA-PK2 | PPA-PK3 | PPA-PK4 |
|---|---|---|---|---|
| PPA-HCl | 0.5 g (6.6%) | 0.5 g (6.1%) | 0.5 g (6.1%) | 0.5 g (6.1%) |
| $K_3PO_4$ | 0 | 0.57 g (7.0%) | 0.6 g (7.3%) | 0.66 g (8.0%) |
| DI water | 1.0 g (13.2%) | 1.0 g (12.2%) | 1.0 g (12.2%) | 1.0 g (12.1%) |
| Propylene glycol | 0.5 g (6.6%) | 0.5 g (6.1%) | 0.5 g (6.1%) | 0.5 g (6.1%) |
| Methyl alcohol | 0.5 g (6.6%) | 0.5 g (6.1%) | 0.5 g (6.1%) | 0.5 g (6.1%) |
| PIB adhesive (30% solid) | 4 g (52.6%) | 4 g (49.0%) | 4 g (48.8%) | 4 g (48.4%) |
| HPMC | 0.1 g (1.3%) | 0.1 g (1.2%) | 0.1 g (1.2%) | 0.1 g (1.2%) |
| Heptane | 1 g (13.2%) | 1 g (12.2%) | 1 g (12.2%) | 1 g (12.1%) |

TABLE 9

Weight and Theoretical Weight Percent of Each Component in the Dried Film for Four PPA-HCl Transdermal Systems

|  | PPA-PK1 | PPA-PK2 | PPA-PK3 | PPA-PK4 |
|---|---|---|---|---|
| PPA-HCl | 0.5 g (21.7%) | 0.5 g (17.4%) | 0.5 g (17.2%) | 0.5 g (16.9%) |
| $K_3PO_4$ | 0 | 0.57 g (19.9%) | 0.6 g (20.7%) | 0.66 g (22.3%) |
| Propylene glycol | 0.5 g (21.7%) | 0.5 g (17.4%) | 0.5 g (17.2%) | 0.5 g (16.9%) |
| PIB adhesive | 1.2 g (52.2%) | 1.2 g (41.8%) | 1.2 g (41.4%) | 1.2 g (40.5%) |
| HPMC | 0.1 g (4.3%) | 0.1 g (3.5%) | 0.1 g (3.4%) | 0.1 g (3.4%) |

TABLE 10

Cumulative Amount of PPA-HCl across human cadaver skin for PPA-HCl Transdermal Systems ($\mu g/cm^2$)

|  | PPA-PK1 | PPA-PK2 | PPA-PK3 | PPA-PK4 |
|---|---|---|---|---|
| 5 hours | 94.7 | 660.0 | 421.6 | 362.9 |
| 16 hours | 445.9 | 1701.3 | 1420.3 | 1607.5 |
| 20 hours | 576.8 | 1919.2 | 1633.1 | 1872.5 |
| 24 hours | 680.5 | 2055.2 | 1762.9 | 2021.1 |

TABLE 11

Excess $K_3PO_4$ Concentration and pH of Four PPA-HCl Transdermal Systems

|  | PPA-PK1 | PPA-PK2 | PPA-PK3 | PPA-PK4 |
|---|---|---|---|---|
| Excess $K_3PO_4$ Concentration (wt. %) | — | 0.2% | 1.2% | 3.2% |
| pH | 6.75 | 9.68 | 9.62 | 10.08 |

The cumulative amount of PPA-HCl that permeated across the human cadaver skin at 24 hours for PPA-PK2 (2055.2 $\mu g/cm^2$, Table 10) with a calculated excess $K_3PO_4$ concentration of 0.2% was three times higher than that from the formulation without $K_3PO_4$ (PPA-PK1, 680.5 $\mu g/cm^2$). This result indicated that the permeation of PPA-HCl could be enhanced with an excess $K_3PO_4$ concentration as low as 0.2%.

The cumulative amount of PPA-HCl across human cadaver skin at 24 hours remained about the same when the excess $K_3PO_4$ concentration in the dried patch was increased from 0.2% to 3.2% (Tables 10 and 11).

The pH of the PPA-HCl patch measured using the procedures listed above increased from 6.75 to 9.68 when the $K_3PO_4$ concentration in the dried patch was increased from 0% to 19.9% (or 0.2% excess $K_3PO_4$ concentration, Tables 9 and 11). However, the pH of the PPA-HCl patch remained about the same when the excess $K_3PO_4$ concentration in the dried patch was further increased from 0.2% to 3.2% (Table 11).

EXAMPLE 4

Figure 4:
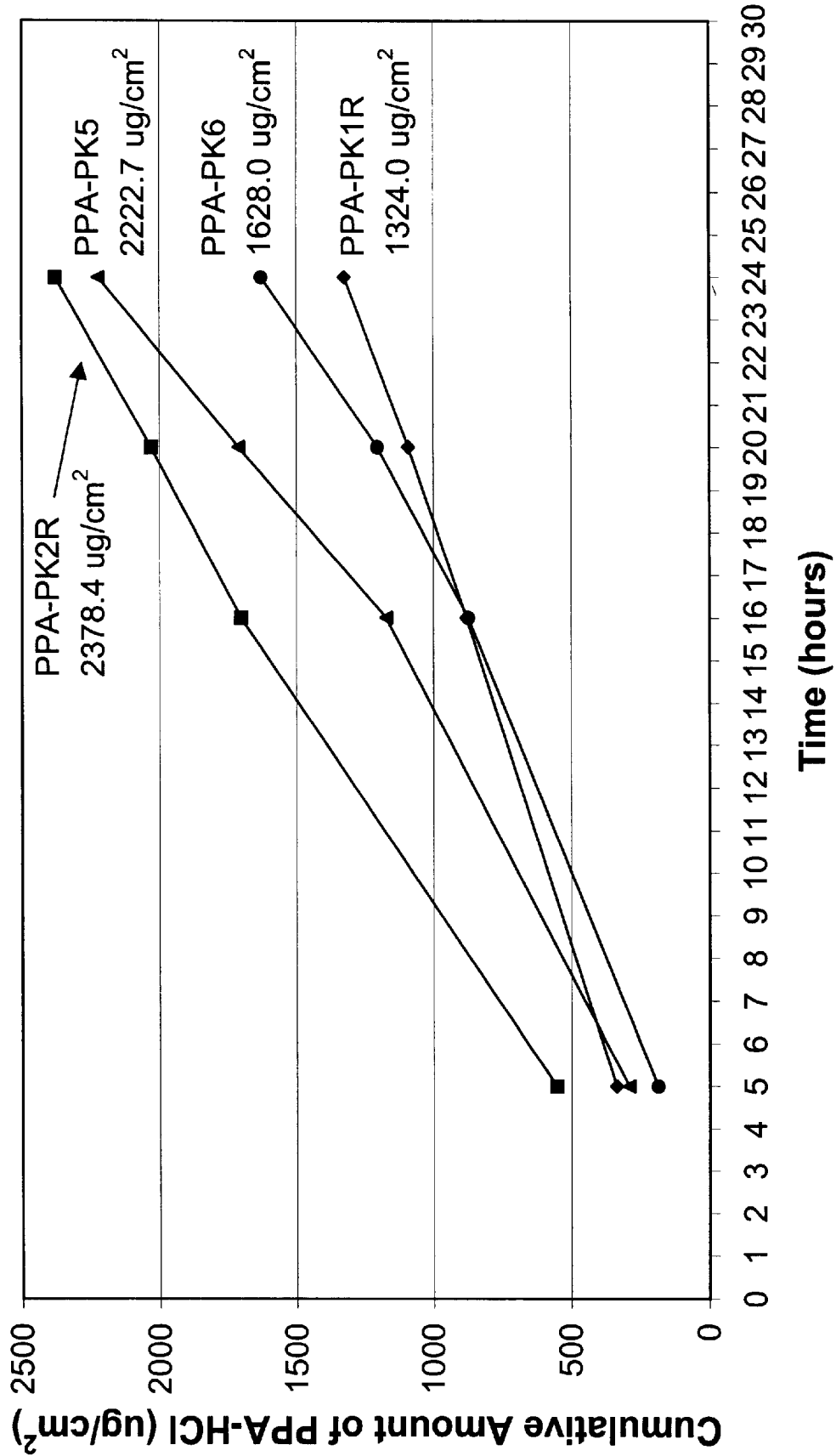
FIG. 4 is a graph illustrating the cumulative amount of racemic phenylpropanolamine permeated from matrix patches as described in Example 4.

An in vitro skin permeation study was conducted using four phenylpropanolamine hydrochloride (PPA-HCl) transdermal systems. The formulations used to prepare these systems are listed in Table 12, which includes weight and weight percent of each component in the formulations. The weight of potassium phosphate, tribasic ($K_3PO_4$) was 0 g, 0.57 g, 0.73 g, and 1.05 g for formulation #PPA-PK1R, -PK2R, -PK5, and -PK6 respectively. The matrix patches were prepared and evaluated using the same procedures as set forth in Example 1. The theoretical percent weight for each ingredient after drying (calculated assuming all the volatile ingredients were completely removed during drying) is listed in Table 13. The cumulative amount of PPA-HCl across human cadaver skin was calculated using the measured PPA-HCl concentrations in the receiver solutions, which were shown in Table 14 and FIG. 4.

The excess $K_3PO_4$ concentration for four PPA-HCl systems, #PPA-PK1R, -PK2R, -PK5 and -PK6 were calculated using the procedure of Example 3 and the results are listed in Table 15. The pH of each patch was determined using the procedure of Example 1 and the results are listed in Table 15.

TABLE 12

Weight and Weight Percent of Each Component (Based on Total Solution Weight) for Four PPA-HCl Transdermal Systems

|  | PPA-PK1R | PPA-PK2R | PPA-PK5 | PPA-PK6 |
|---|---|---|---|---|
| PPA-HCl | 0.5 g (6.9%) | 0.5 g (6.4%) | 0.5 g (6.3%) | 0.5 g (6.1%) |
| $K_3PO_4$ | 0 | 0.57 g (7.3%) | 0.73 g (9.2%) | 1.05 g (12.7%) |
| DI water | 1.0 g (13.9%) | 1.0 g (12.9%) | 1.0 g (12.6%) | 1.0 g (12.1%) |
| Methyl alcohol | 0.5 g (6.9%) | 0.5 g (6.4%) | 0.5 g (6.3%) | 0.5 g (6.1%) |
| Propylene glycol | 0.2 g (2.8%) | 0.2 g (2.6%) | 0.2 g (2.5%) | 0.2 g (2.4%) |
| HPMC | 0.01 g (0.1%) | 0.01 g (0.1%) | 0.01 g (0.1%) | 0.01 g (0.1%) |
| Heptane | 1 g (13.9%) | 1 g (12.9%) | 1 g (12.6%) | 1 g (12.1%) |
| PIB adhesive (30% solid) | 4 g (55.5%) | 4 g (51.4%) | 4 g (50.4%) | 4 g (48.4%) |

TABLE 13

Weight and Theoretical Weight Percent of Each Component in the Dried Film for Four PPA-HCl Transdermal Systems

|  | PPA-PK1R | PPA-PK2R | PPA-PK5 | PPA-PK6 |
|---|---|---|---|---|
| PPA-HCl | 0.5 g (26.2%) | 0.5 g (20.2%) | 0.5 g (18.9%) | 0.5 g (16.5%) |
| $K_3PO_4$ | 0 | 0.57 g (23.6%) | 0.73 g (27.7%) | 1.05 g (35.5%) |
| Propylene glycol | 0.2 g (10.5%) | 0.2 g (8.1%) | 0.2 g (7.6%) | 0.2 g (6.8%) |
| HPMC | 0.01 g (0.5%) | 0.01 g (0.4%) | 0.01 g (0.4%) | 0.01 g (0.3%) |
| PIB adhesive | 1.2 g (62.8%) | 1.2 g (48.4%) | 1.2 g (45.5%) | 1.2 g (40.5%) |

TABLE 14

Cumulative Amount of PPA-HCl across human cadaver skin for PPA-HCl Transdermal Systems ($\mu g/cm^2$)

|  | PPA-PK1R | PPA-PK2R | PPA-PK5 | PPA-PK6 |
|---|---|---|---|---|
| 5 hours | 336.8 | 553.1 | 291.5 | 186.7 |
| 16 hours | 879.5 | 1702.4 | 1172.5 | 873.1 |
| 20 hours | 1091.2 | 2031.2 | 1711.5 | 1204.3 |
| 24 hours | 1324.0 | 2378.4 | 2222.7 | 1628.0 |

TABLE 15

Excess $K_3PO_4$ Concentration and pH of Four PPA-HCl Transdermal Systems

|  | PPA-PK1R | PPA-PK2R | PPA-PK5 | PPA-PK6 |
|---|---|---|---|---|
| Excess $K_3PO_4$ Concentration (wt. %) |  | 0.2% | 6.2% | 16.4% |
| pH | 7 | 9.72 | 10.17 | 10.44 |

The cumulative amount of PPA-HCl that permeated across the human cadaver skin at 24 hours for PPA-PK2R (2378.4 $\mu g/cm^2$, Table 14) with a calculated excess $K_3PO_4$ concentration of 0.2% was about two times higher than that from the formulation without $K_3PO_4$ (PPA-PK1R, 1324.0 $\mu g/cm^2$). This result indicated that the permeation of PPA-HCl is enhanced with an excess $K_3PO_4$ concentration as low as 0.2%.

The cumulative amount of PPA-HCl across human cadaver skin at 24 hours remained about the same when the excess $K_3PO_4$ concentration in the dried patch was increased from 0.2% to 6.2% (Tables 14 and 15). When the excess $K_3PO_4$ concentration in the dried patch was further increased from 6.2% to 16.4% (Table 15), the cumulative amount of PPA-HCl across human cadaver skin at 24 hours decreased from 2222.7 to 1628.0 $\mu g/cm^2$. This decrease in flux may be because the high concentration of $K_3PO_4$ made the adhesive matrix more hydrophobic and the amount of $K_3PO_4$ that could be dissolved by the small amount of water on the top of the skin was reduced.

The pH of the PPA-HCl patch measured using the procedures listed above increased from 7 to 9.72 when the $K_3PO_4$ concentration in the dried patch was increased from 0% to 23% (or 0.2% excess $K_3PO_4$ concentration, Tables 13 and 15). The pH of the PPA-HCl patch increased from 9.72 to 10.44 when the excess $K_3PO_4$ concentration in the dried patch was further increased from 0.2% to 16.4% (Table 15).

EXAMPLE 5

Figure 5:
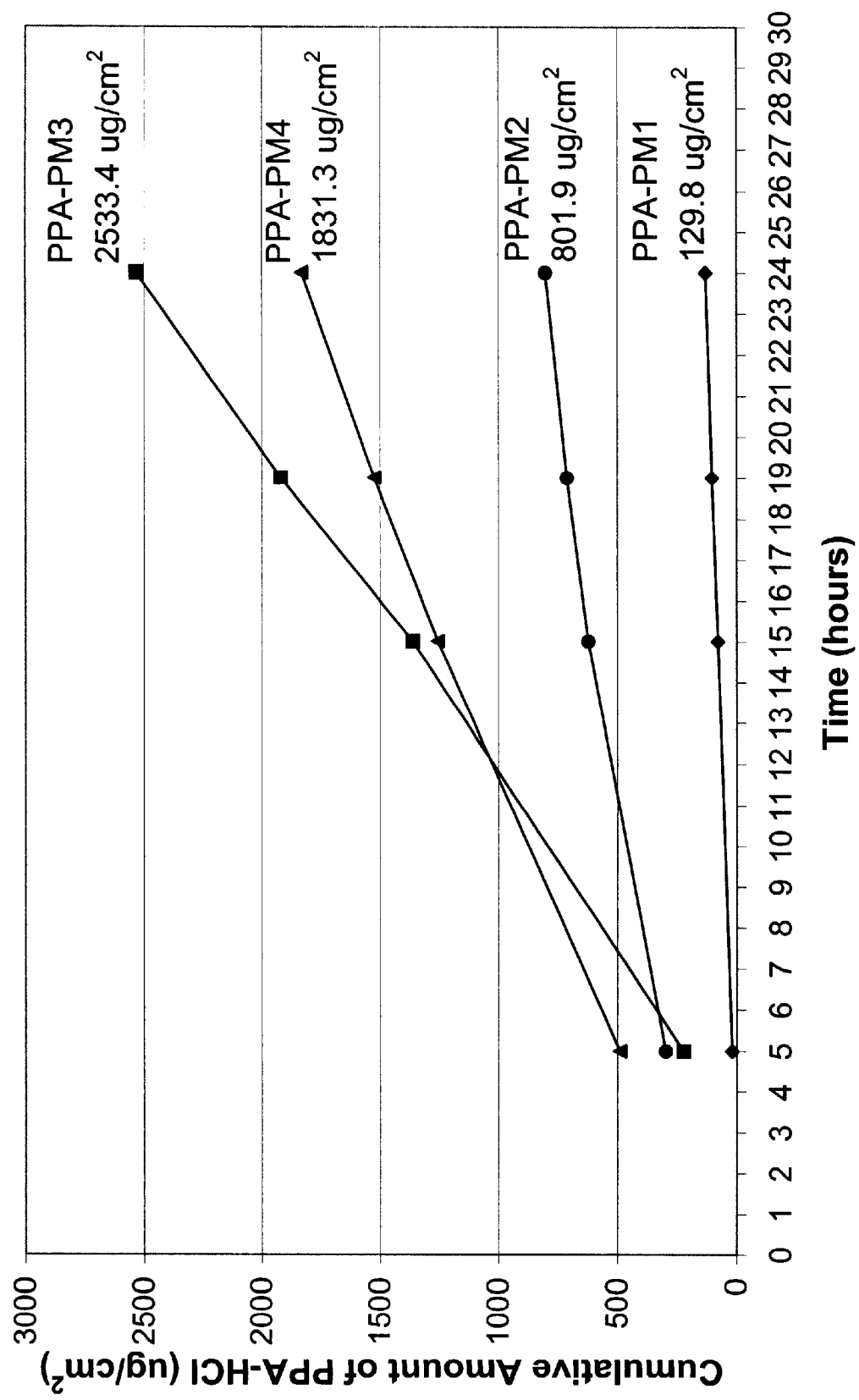
FIG. 5 is a graph illustrating the cumulative amount of racemic phenylpropanolamine permeated from matrix patches as described in Example 5.

An in vitro skin permeation study was conducted using four phenylpropanolamine hydrochloride (PPA-HCl) transdermal systems. The formulations used to prepare these systems are listed in Table 16, which includes weight and weight percent of each component in the formulations. The weight of magnesium oxide (MgO) was 0 g, 0.11 g, 0.26 g and 0.50 g for formulation #PPA-PM1, -PM2,-PM3, and -PM4 respectively. The matrix patches were prepared and evaluated using the same procedures as set forth in Example 1. The theoretical percent weight for each ingredient after drying (calculated assuming all the volatile ingredients were completely removed during drying) is listed in Table 17. The cumulative amount of PPA-HCl across human cadaver skin was calculated using the measured PPA-HCl concentrations in the receiver solutions, which were shown in Table 18 and FIG. 5.

Since PPA-HCl is a salt of a free base, it reacts with MgO. The concentration of MgO in the system after the reaction is completed depends on the amount of PPA-HCl added. The remaining MgO concentration after the reaction is completed is defined as "excess MgO concentration," which is calculated by the following equation.

$$[MgO_{excess}] = [MgO_{total}] - [MgO_{needed\ for\ neutralization}]$$

The excess MgO concentration for four PPA-HCl systems, #PPA-PM1, -PM2, -PM3 and -PM4 were calculated and listed in Table 19.

The pH of the patch was determined using the procedure of Example 1 and the results are listed in Table 19.

TABLE 16

Weight and Weight Percent of Each Component (Based on Total Solution Weight) for Four PPA-HCl Transdermal Systems

|  | PPA-PM1 | PPA-PM2 | PPA-PM3 | PPA-PM4 |
|---|---|---|---|---|
| PPA-HCl | 0.5 g (6.9%) | 0.5 g (6.0%) | 0.5 g (5.9%) | 0.5 g (5.7%) |
| MgO | 0 | 0.11 g (1.3%) | 0.26 g (3.1%) | 0.50 g (5.7%) |
| DI water | 1.0 g (13.9%) | 2.0 g (24.0%) | 2.0 g (23.6%) | 2.0 g (22.9%) |
| Methyl alcohol | 0.5 g (6.9%) | 0.5 g (6.0%) | 0.5 g (5.9%) | 0.5 g (5.7%) |
| Propylene glycol | 0.2 g (2.8%) | 0.2 g (2.4%) | 0.2 g (2.4%) | 0.2 g (2.3%) |
| HPMC | 0.02 g (0.3%) | 0.02 g (0.2%) | 0.02 g (0.2%) | 0.02 g (0.02%) |
| PIB adhesive (30% solid) | 4 g (55.4%) | 4 g (48.0%) | 4 g (47.2%) | 4 g (45.9%) |
| Heptane | 1.0 g (13.9%) | 1.0 g (12.0%) | 1.0 g (11.8%) | 1.0 g (11.5%) |

TABLE 17

Weight and Theoretical Weight Percent of Each Component in the Dried Film for Four PPA-HCl Transdermal Systems

|  | PPA-PM1 | PPA-PM2 | PPA-PM3 | PPA-PM4 |
|---|---|---|---|---|
| PPA-HCl | 0.5 g (26.0%) | 0.5 g (24.6%) | 0.5 g (22.9%) | 0.5 g (20.7%) |
| MgO | 0 | 0.11 g (5.4%) | 0.26 g (11.9%) | 0.50 g (20.7%) |
| Propylene glycol | 0.2 g (10.4%) | 0.2 g (9.9%) | 0.2 g (9.2%) | 0.2 g (8.3%) |
| HPMC | 0.02 g (1.0%) | 0.02 g (1.0%) | 0.02 g (0.9%) | 0.02 g (0.8%) |
| PIB adhesive | 1.2 g (62.5%) | 1.2 g (59.1%) | 1.2 g (55.0%) | 1.2 g (49.6%) |

TABLE 18

Cumulative Amount of PPA-HCl Across Human Cadaver Skin for PPA-HCl Transdermal Systems ($\mu g/cm^2$)

|  | PPA-PM1 | PPA-PM2 | PPA-PM3 | PPA-PM4 |
|---|---|---|---|---|
| 5 hours | 18.7 | 296.8 | 222.1 | 489.4 |
| 15 hours | 77.8 | 621.5 | 1362.9 | 1255.2 |
| 19 hours | 102.7 | 711.4 | 1920.9 | 1524.9 |
| 24 hours | 129.8 | 801.9 | 2533.4 | 1831.3 |

TABLE 19

Excess MgO Concentration and pH of Four PPA-HCl Transdermal Systems

|  | PPA-PM1 | PPA-PM2 | PPA-PM3 | PPA-PM4 |
|---|---|---|---|---|
| Excess MgO Concentration (wt. %) |  | 0.1% | 7.0% | 16.2% |
| pH | 7.89 | 9.60 | 10.09 | 10.10 |

The cumulative amount of PPA-HCl that permeated across the human cadaver skin at 24 hours for PPA-PM2 (801.9 $\mu g/cm^2$, Table 18) with a calculated excess MgO concentration of 0.1% was about six times higher than that from the formulation without MgO (PPA-PM1, 129.8 $\mu g/cm^2$). This result indicated that the permeation of PPA-HCl is enhanced with an excess MgO concentration as low as 0.1%.

The cumulative amount of PPA-HCl across human cadaver skin at 24 hours increased from 801.9 to 2533.4 $\mu g/cm^2$ when the excess MgO concentration in the dried patch was increased from 0.1% to 7.0% (Tables 18 and 19). When the excess MgO concentration in the dried patch was further increased from 7.0% to 16.2% (Table 19), the cumulative amount of PPA-HCl across human cadaver skin at 24 hours decreased from 2533.4 to 1831.3 $\mu g/cm^2$. This decrease in flux may be because the high concentration of MgO made the adhesive matrix more hydrophobic and the amount of MgO that could be dissolved by the small amount of water on the top of the skin was reduced.

The pH of the PPA-HCl patch measured using the procedures listed above increased from 7.89 to 9.60 when the MgO concentration in the dried patch was increased from 0% to 5.4% (or 0.1% excess MgO concentration, Tables 17 and 19). The pH of the PPA-HCl remained about the same when the excess MgO concentration in the dried patch was further increased from 0.1% to 16.2% (Table 19).

We claim:

1. A method for treating an individual suffering from or susceptible to condition, disorder or disease that is responsive to administration of phenylpropanolamine, comprising administering a therapeutically effective amount of racemic phenylpropanolamine to a localized region of a human patient's body surface, in combination with an effective permeation-enhancing amount of a hydroxide-releasing agent selected from the group consisting of ammonium hydroxide, alkali metal hydroxides, alkaline earth metal hydroxides, magnesium oxide, calcium oxide, and mixtures thereof.

2. The method of claim 1, wherein the racemic phenylpropanolamine is a mixture of two or more of (+)-norephedrine, (−)-norephedrine, (+)-norpseudoephedrine, and (−)-norpseudoephedrine.

3. The method of claim 2, wherein the racemic phenylpropanolamine is a mixture of (−)-norephedrine and (+)-norephedrine.

4. The method of claim 3, wherein at least about 50% of the phenylpropanolamine is present in uncharged, free base form.

5. The method of claim 4, wherein at least about 75% of the phenylpropanolamine is present in uncharged, free base form.

6. The method of claim 5, wherein at least about 90% of the phenylpropanolamine is present in uncharged, free base form.

7. The method of claim 6, wherein at least about 95% of the phenylpropanolamine is present in uncharged, free base form.

8. The method of claim 1, wherein the racemic phenylpropanolamine is administered along with an additional permeation enhancer.

9. The method of claim 1, wherein the hydroxide-releasing agent is applied in an amount effective to provide a pH in the range of approximately 8.0 to 13 at the localized region of the body surface, during drug administration.

10. The method of claim 9, wherein the pH is in the range of approximately 8.0 to 11.5.

11. The method of claim 1, wherein the body surface is skin.

12. The method of claim 1, wherein the body surface is mucosal tissue.

13. The method of claim 1, wherein the phenylpropanolamine and the hydroxide-releasing agent are applied to the body surface simultaneously.

14. The method of claim 1, wherein the phenylpropanolamine and the hydroxide-releasing agent are present in a single pharmaceutical formulation.

15. The method of claim 14, wherein the formulation is aqueous.

16. The method of claim 15, wherein the formulation has a pH in the range of approximately 8.0 to 13.

17. The method of claim 16, wherein the pH is in the range of approximately 8.0 to 11.5.

18. The method of claim 15, wherein the aqueous formulation is selected from the group consisting of a cream, a gel, a lotion, and a paste.

19. The method of claim 18, wherein the formulation is a cream.

20. The method of claim 18, wherein the formulation is a gel.

21. The method of claim 14, wherein the formulation is nonaqueous.

22. The method of claim 21, wherein the formulation is an ointment.

23. The method of claim 1, wherein the hydroxide-releasing agent is administered to the localized region of body surface prior to administration of the active agent, wherein the hydroxide-releasing agent is in a solution comprised of a protic solvent having a pH in the range of approximately 8.0 to 13.

24. The method of claim 4, wherein the hydroxide-releasing agent is selected from the group consisting of ammonium hydroxide, alkali metal hydroxides, alkaline earth metal hydroxides, and mixtures thereof.

25. The method of claim 24, wherein the hydroxide-releasing agent is selected from the group consisting of ammonium hydroxide, sodium hydroxide, calcium hydroxide, potassium hydroxide, magnesium hydroxide, and mixtures thereof.

26. The method of claim 25, wherein the hydroxide-releasing agent is sodium hydroxide.

27. The method of claim 25, wherein the hydroxide-releasing agent is potassium hydroxide.

28. The method of claim 14, wherein the hydroxide-releasing agent is selected from the group consisting of magnesium oxide, calcium oxide, and mixtures thereof.

29. The method of claim 28, wherein the amount of hydroxide-releasing agent in the formulation is the total of (a) the amount required to neutralize any salts and acidic species in the formulation plus (b) an amount equal to approximately 0.5 wt. % to 4.0 wt. % of the formulation.

30. The method of claim 29, wherein the amount of hydroxide-releasing agent in the formulation is the total of (a) the amount required to neutralize any salts and acidic species in the formulation plus (b) an amount equal to approximately 0.5 wt. % to 3.0 wt. % of the formulation.

31. The method of claim 30, wherein the amount of hydroxide-releasing agent in the formulation is the total of (a) the amount required to neutralize any salts and acidic species in the formulation plus (b) an amount equal to approximately 0.75 wt. % to 2.0 wt. % of the formulation.

32. The method of claim 31, wherein the amount of hydroxide-releasing agent in the formulation is the total of (a) the amount required to neutralize any salts and acidic species in the formulation plus (b) an amount equal to approximately 1.0 wt. % of the formulation.

33. The method of claim 29, wherein the active agent is in the form of an acid addition salt, and the amount in (a) is the amount required to neutralize the acid addition salt and any other acidic species in the formulation.

34. The method of claim 28, wherein the formulation contains up to approximately 25 wt. % of the hydroxide-releasing agent.

35. The method of claim 34, wherein the formulation contains up to approximately 20 wt. % of the hydroxide-releasing agent.

36. The method of claim 1, wherein the racemic phenylpropanolamine and the hydroxide-releasing agent are administered by applying a drug delivery device to the localized region of the patient's body surface thereby forming a body surface-delivery device interface, the device comprising the racemic phenylpropanolamine and the hydroxide-releasing agent, and having an outer backing layer that serves as the outer surface of the device during use.

37. The method of claim 36, wherein the outer backing layer is occlusive.

38. The method of claim 37, wherein the pH at the interface is in the range of approximately 8.0 to 13.

39. The method of claim 38, wherein the pH at the interface is in the range of approximately 8.0 to 11.5.

40. The method of claim 36, wherein the racemic phenylpropanolamine is administered in combination with an additional permeation enhancer.

41. The method of claim 1, wherein the racemic phenylpropanolamine and the hydroxide-releasing agent are administered without any additional permeation enhancer.

42. A device for the transdermal administration of racemic phenylpropanolamine, comprising:

(a) at least one drug reservoir containing the racermic phenylpropanolamine and a hydroxide-releasing agent in an amount effective to enhance the flux of the drug through the body surface without causing damage thereto, wherein the hydroxide-releasing agent is selected from a group consisting of ammonium hydroxide, alkali metal hydroxides, alkaline earth metal hydroxides, magnesium oxide, calcium oxide, and mixtures thereof, (b) a means for maintaining the device in drug- and enhancer-transmitting relationship to the body surface; and (c) a backing layer that serves as the outer surface of the device during use.

43. The system of claim 42, wherein the racemic phenylpropanolamine is a mixture of two or more of (+)-norephedrine, (−)-norephedrine, (+)-norpseudoephedrine, and (−)-norpseudoephedrine.

44. The system of claim 43, wherein the racemic phenylpropanolamine is a mixture of (−)-norephedrine and (+)-norephedrine.

45. The system of claim 42, wherein the drug reservoir is comprised of a polymeric adhesive.

46. The system of claim 45, wherein the polymeric adhesive serves as the means for maintaining the system in drug and enhancer transmitting relationship to the body service.

47. The system of claim 42, wherein the drug reservoir is comprised of a hydrogel.

48. The system of claim 42, wherein the drug reservoir is comprised of a sealed pouch containing the drug and hydroxide-releasing agent in a liquid or semi-solid formulation.

* * * * *

UNITED STATES PATENT AND TRADEMARK OFFICE
CERTIFICATE OF CORRECTION

PATENT NO. : 6,602,912 B2
DATED : August 5, 2003
INVENTOR(S) : Tsung-Min Hsu et al.

It is certified that error appears in the above-identified patent and that said Letters Patent is hereby corrected as shown below:

Column 30,
Line 23, please delete "active agent" and insert -- racemic phenylpropanolamine --.

Column 31,
Lines 6 and 10, please delete "system" and insert -- device --.

Column 32,
Lines 1, 3, 4, 7 and 9, please delete "system" and insert -- device --.
Line 10, please delete "drug" and insert -- racemic phenylpropanolamine --.

Signed and Sealed this

Twenty-third Day of December, 2003

JAMES E. ROGAN
*Director of the United States Patent and Trademark Office*